(12) United States Patent
Burger et al.

(10) Patent No.: US 6,407,437 B1
(45) Date of Patent: *Jun. 18, 2002

(54) MICROMECHANICAL PIPETTING DEVICE

(75) Inventors: Jürgen Burger, Ipsach; Felix Baader, Menzingen; Rudolf Buser, Zurich; Olivier Elsenhans, Jonen; Nicolas Szita, Zurich, all of (CH)

(73) Assignee: Roche Diagnostics Corporation, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/044,735

(22) Filed: Mar. 19, 1998

(30) Foreign Application Priority Data

Mar. 20, 1997 (EP) ............................................. 97104756

(51) Int. Cl.⁷ ............................................. H01L 29/84
(52) U.S. Cl. ...................... 257/415; 257/414; 92/103 R
(58) Field of Search ........................ 92/103 R; 257/414, 257/415

(56) References Cited

U.S. PATENT DOCUMENTS 5,591,139 A * 1/1997 Lin et al. ..................... 257/414

FOREIGN PATENT DOCUMENTS

EP 0 725 267 8/1996

OTHER PUBLICATIONS

Gravesen et al., Journal of Micromechanics & Microengineering, vol. 3, pp. 168–182 (1993).
Patent Abstracts of Japan, pub. No. 07213926, vol. 095, No. 011 (1995).
Patent Abstracts of Japan, pub. No. 08219956, vol. 096, No. 012 (1996).
Patent Abstracts of Japan, pub. No. 08290377, vol. 097, No. 003 (1997).
Derwent Abstract, accession No. 10859238.
Lammerink et al., IEEE, pp. 254–259 (1993).
Schober et al., BioTechniques, vol. 15, No. 2, pp. 324–329 (1993).

* cited by examiner

Primary Examiner—Jerome Jackson, Jr.
(74) Attorney, Agent, or Firm—Gibbons, Del Deo, Dolan Griffinger & Vecchione

(57) ABSTRACT

A micromechanical pipetting device comprising an integrally built pipetting module which has an inlet/outlet which may be connected to a removable pipetting tip or integrally built with a pipetting tip. The pipetting module comprises a micromechanical structure which is integrally built on a silicon wafer. In order to improve the accuracy of the pipetted volume the device is characterized in that it comprises a) a first chamber located within said pipetting module, the volume comprised within said first chamber being alterable by displacement of a membrane which is a portion of a wall of said chamber, said first chamber having an opening, said opening being permanently open and allowing fluid flow into and from the interior of said first chamber, b) a channel located within said pipetting module, said channel establishing a direct, valveless and permanent fluidical connection between said opening of the first chamber and the inlet/outlet of the pipetting module, c) actuator means for displacing said membrane, and thereby aspiring or expelling a volume of air or of a liquid into or from said first chamber, which in turn causes aspiring or expelling a volume of a liquid sample into respectively from said pipetting tip, and d) first sensor means for generating a first output signal related to the displacement of the membrane.

27 Claims, 6 Drawing Sheets

MICROMECHANICAL PIPETTING DEVICE

BACKGROUND OF THE INVENTION

The invention relates to a micromechanical pipetting device for pipetting liquid volumes in a range between a minimum value smaller than a microliter and a maximum value of about 10 microliters. The device comprises a pipetting module which has an inlet/outlet which may either be connected to a removable pipetting tip or may have a pipetting tip integrally built into the module. The integrally built pipetting module comprises a micromechanical structure which is integrally built on a silicon wafer.

Some micromechanical structures are known for the purpose of dispensing very small volumes of liquid. A micromechanical pump comprising valves can be used for this purpose, but high accuracy of the dispensed volumes cannot be attained, mainly due to the reflow caused by the operation of the valves and dead volumes and leaking problems associated with the use of valves. Moreover such micropumps normally pump a number of liquid portions until the desired volume to be dispensed is approximately attained. Thus the accuracy of the total volume dispensed depends from the accuracy of the volume portion transported by each pumping step.

A similar approach can also be implemented by dispensing microdrops, as in ink-jet printers, until the desired volume to be dispensed is approximately attained. Also in this case the accuracy of the total volume dispensed depends from the accuracy of the volume of each microdrop. The accuracy of pipetted volume obtained by this approach is limited, in particular because it depends on the properties of the liquid being pipetted.

Another known approach for dispensing very small volumes of liquid is the use of a micromechanical pump controlled by a feedback loop comprising an anemometric flow sensor and an integrator of the output signal of this sensor. The function of the feedback loop is to measure the volume pumped by the micromechanical pump and to control it accordingly. Thus in theory the feedback loop would control the micromechanical pump in such a way that the latter pumps a steady flow of liquid over an interval of time until the desired volume to be dispensed is attained and then the operation of the pump is stopped. This approach has several important disadvantages. There is always a delay between the measurement of the pumped volume and a corresponding control of the micromechanical pump. Thus a correction of the operation of the pump via feedback loop only happens after the pumped volume is already larger than the desired value. Such a device is therefore not accurate enough for pipetting very small volumes with high accuracy. The operation of anemometric flow sensors requires heating of the liquid pumped. Thus, such a device cannot be used for pumping thermally sensitive liquids of the kind to be pipetted e.g. in clinical chemistry analyzers.

SUMMARY OF THE INVENTION

The aim of the invention is therefore to provide a micromechanical pipetting device for pipetting with high accuracy very small volumes of liquids and with which the above-mentioned disadvantages of known prior art devices can be avoided.

According to the invention, this aim is attained with a device of the type described herein, which device is characterized in that it comprises.

a) a first chamber located within a pipetting module, wherein the volume contained within said first chamber may be modified by displacement of a membrane which is a portion of a wall of said chamber, said first chamber having only one opening, said opening being permanently open and allowing fluid flow into and from the interior of said first chamber, b) a channel located within said pipetting module, said channel establishing a direct, valveless and permanent fluidical connection between said opening of the first chamber and the inlet/outlet of the pipetting module, c) actuator means for displacing said membrane, and thereby aspirating or expelling a volume of air or of a liquid into or from said first chamber, which in turn causes aspiration or expulsion of a volume of a liquid sample through said pipetting tip, and d) a first sensor means for generating a first output signal related to the displacement of the membrane.

The main advantage of the device according to the invention as compared with the prior art devices is that it makes it possible to pipette very small volumes of liquid with high accuracy, reproducibility, reliability and fast performance.

In particular the inclusion of a first sensor means for generating a first output signal related to the displacement of the membrane makes possible a highly accurate and real-time monitoring of the operation of the device which is suitable for the fast forward and reverse flow in a pipetting device according to the invention.

Moreover, the device according to the invention advantageously differs from prior art devices in that it makes it possible to pipette the entire volume to be pipetted by a single stroke of the actuator means.

A preferred embodiment of the device according to the invention further comprises a control means for controlling the operation of the actuator means in response to the first output signal generated by the first sensor means. The micropipetting module according to the invention and the means for controlling the operation of the actuator means are preferrably configured and dimensioned so that the total volume to be aspirated and dispensed with the pipetting tip is aspirated into the pipetting tip by means of a single stroke of the displacement movement of the membrane.

Another preferred embodiment of the device according to the invention is characterized in that a portion of the membrane is part of the first sensor means and the first output signal generated by this sensor means is related to or representative of the displacement of the membrane.

A further preferred embodiment of the device according to the invention is characterized in that a portion of the channel forms a second chamber and is part of a second sensor means for generating a second output signal representative of the pressure in the channel, and the means for controlling the operation of the actuator means is responsive to both the first and the second output signals.

A further preferred embodiment of the device according to the invention is characterized in that a portion of the channel forms a second chamber and is part of a second sensor means for generating a second output signal representative of the fluid flow through the channel, and the means for controlling the operation of the actuator means is responsive to both the first and the second output signals.

The above mentioned preferred embodiments which include the association of multifunctional sensors located close to the pipetting tip make possible a direct and highly accurate monitoring of very small pipetted volumes and early and active recognition and avoidance of malfunctions of the micropipetting module.

A further preferred embodiment of the device according to the invention is characterized in that a portion of the channel forms a third chamber which is located between the pipetting tip and the first or the second sensor means, said third chamber serving to prevent pipetted fluid from contacting the portion of the channel which comprises said first sensor means or said second sensor means.

A further preferred embodiment of the device according to the invention is characterized in that said actuator means comprises an electrostatic actuator or a piezoelectric actuator or an electromechanical actuator.

A further preferred embodiment of the device according to the invention is characterized in that said first sensor means is a capacitive or an electro-optical sensor.

A further preferred embodiment of the device according to the invention is characterized in that said second sensor means comprises a pressure or a flow measurement sensor. The use of an integrated pressure sensor according to the instant invention ensures that the pipetting module operates in the normal range (e.g. of viscosity) for which the system is designed.

A further preferred embodiment of the device according to the invention is characterized in that a plurality of said pipetting modules is integrally built on a silicon wafer.

A further preferred embodiment of the device according to the invention is characterized in that the pipetting tip is a silicon pipetting tip integrally built with the pipetting module.

Exemplified embodiments of the invention are described below with reference to the accompanying drawings.

DETAILED DESCRIPTION OF THE INVENTION

Figure 1A:
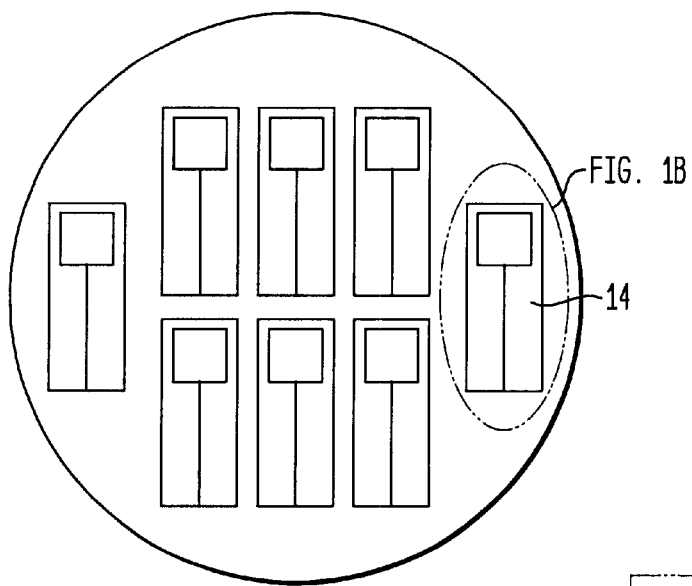
FIG. 1a is a schematic view of an array of micromechanical modules formed on a silicon wafer.

FIG. 1a shows schematically a silicon wafer on which an array of micromechanical modules 14 has been formed. Each of such modules can be used as a component of a first embodiment of a micromechanical pipetting module according to the invention.

Figure 1B:
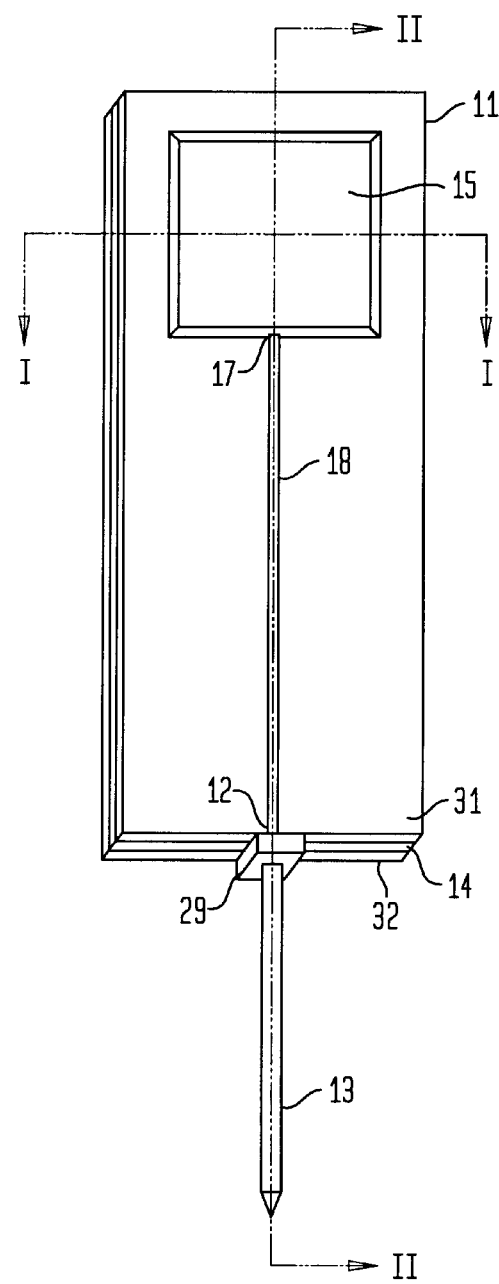
FIG. 1b is a schematic view of a micromechanical pipetting module according to the invention.

FIG. 1b shows schematically a first embodiment 11 of a micromechanical pipetting module according to the invention. Liquid volumes in a range between a minimum value smaller than a microliter and a maximum value of about 10 microliters can be pipetted with such a module. Module 11 is an integrally built pipetting module comprising a micromechanical structure which is integrally built on a silicon wafer 14.

The micromechanical pipetting module 11 shown by FIG. 1b comprises three layers arranged one above the other and connected to one another unreleasably by means of anodic bonding: a first glass layer 31, a second glass layer 32 and a silicon wafer layer 14 arranged between glass layers 31 and 32. Silicon wafer layer 14 is unreleasably connected to glass layers 31 and 32 by means of anodic bonding. Silicon wafer layer 14 in FIG. 1b has a surface of approximately 25×10 mm for the smaller volumes of the target range (minimum value smaller than a microliter and a maximum value of about 10 microliters).

Silicon wafer layer 14 comprises a chamber 15 and a channel 18 formed by micromachining on wafer 14. The bottom wall of chamber 15 is a membrane 16 which is part of silicon wafer 14. Chamber 15 has only one opening 17 which is connected to one end of channel 18. The opposite end of channel 18 forms an inlet/outlet 12 of pipetting module 11. A pipetting tip 13 is connected to inlet/outlet 12 by means of a sealing film 29.

In an alternative embodiment layers 31 and 32 are also fabricated in silicon. This offers the advantage of reducing undesirable temperature effects. In this alternative embodiment the bonding process is called "silicon direct bonding". The disadvantage of this kind of bonding as compared with anodic bonding with glass wafers is the higher temperature needed for performing the bonding process. A compromise to overcome this difficulty is to sputter a thin layer of pyrex glass onto a silicon wafer and then to perform anodic bonding. Within the scope of the invention the material of layers 31 and 32 can thus be either glass or silicon, whereby for silicon two different bonding processes are possible.

Figure 2:
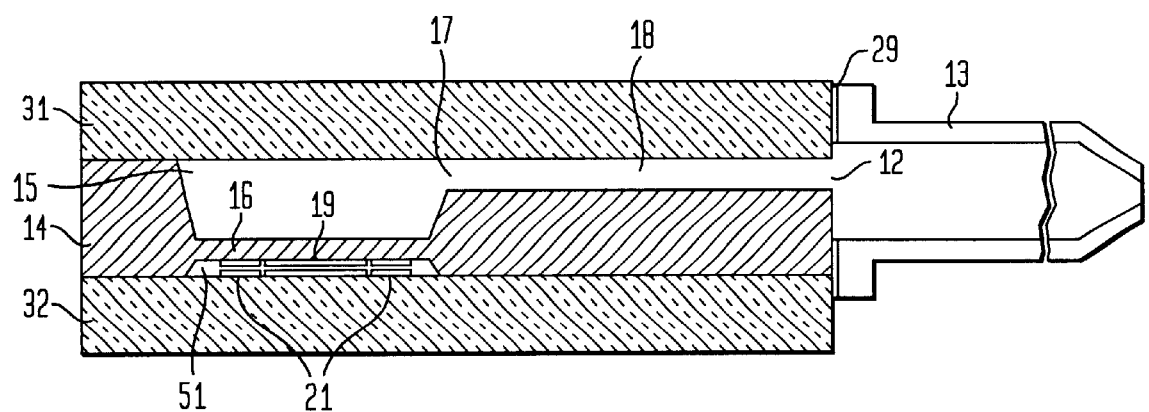
FIG. 2 is a schematic representation of a longitudinal section along the line II—II in FIG. 1b.

FIG. 2 shows a longitudinal section on the line II—II in FIG. 1b. As shown by FIG. 2 a micromechanical pipetting module 11 shown by FIG. 1b comprises chamber 15 having membrane 16 as bottom wall, channel 18, actuator means 19 for displacing membrane 16 and sensor means 21 for generating an output signal related to the displacement of the membrane 16. A portion of the membrane 16 is part of the sensor means 21 and the output signal generated by this sensor means is representative of the displacement of the membrane 16. Components of sensor 21 are located in a chamber 51 delimited by membrane 16, silicon wafer 14 and glass plate 32.

Sensor 21 is preferably a displacement sensor. Sensor 21 in FIG. 2 may comprise an electrical capacitor as measuring element. Sensor 21 in FIG. 2 may alternatively be an electro-optical sensor.

The volume contained within chamber 15 may be increased or decreased by displacement of a membrane 16. Chamber 15 has only one opening 17 which is permanently open and which allows fluid flow into and out of the interior of chamber 15.

Channel 18 establishes a direct, valveless and permanent fluidical connection between opening 17 of chamber 15 and the inlet/outlet 12 of the pipetting module 11.

Actuator means 19 may be an electrostatic actuator as schematically represented in FIG. 2, or a piezoelectric actuator. The electrical connections of actuator 19 are not shown in the Figures. Membrane 16 can also be displaced by a pressure increase or decrease of a gas in the chamber formed by membrane 16, silicon wafer 14 and glass plate 32. This pressure change can be achieved on the chip e.g. by a thermopneumatical actuation, that is by heating and cooling a gas or by evaporation and condensing of a liquid.

Figure 3:
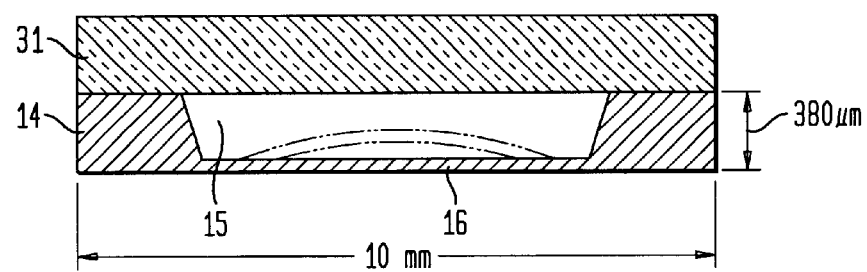
FIG. 3 is a partial representation of a cross-section along the line I—I in FIG. 1b.

FIG. 3 shows a partial representation of a cross-section on the line I—I in FIG. 1b. FIG. 3 shows in particular the cross-sectional shape of chamber 15 and an example of the width and depth of wafer layer 14 of pipetting module 11. The broken line in FIG. 3 shows the position taken by the membrane 16 when it is displaced e.g. by means of an actuator located below membrane 16, but not represented in FIG. 3.

In order to perform a pipetting operation with the pipetting module 11, actuator means 19 are activated to displace membrane 16 for aspirating or expelling a volume of air or of a liquid into or from chamber 15. Such a displacement of membrane 16 causes a corresponding aspiration or expulsion of a volume of a liquid sample from said pipetting tip 13.

When a pipetting module according to the invention is used to perform pipetting operations the interior of the pipetting module is filled either with air or with a liquid, e.g. water, separated from the pipetted liquid by an air segment. Sample or reagent is aspirated or expelled from the pipetting tip when actuator 19 displaces membrane 16. While pipetting, the pipetted liquid, for instance a biological liquid sample or a reagent for performing a clinical chemistry test, does not enter channel 18 but remains within the pipetting tip.

Figure 4A:
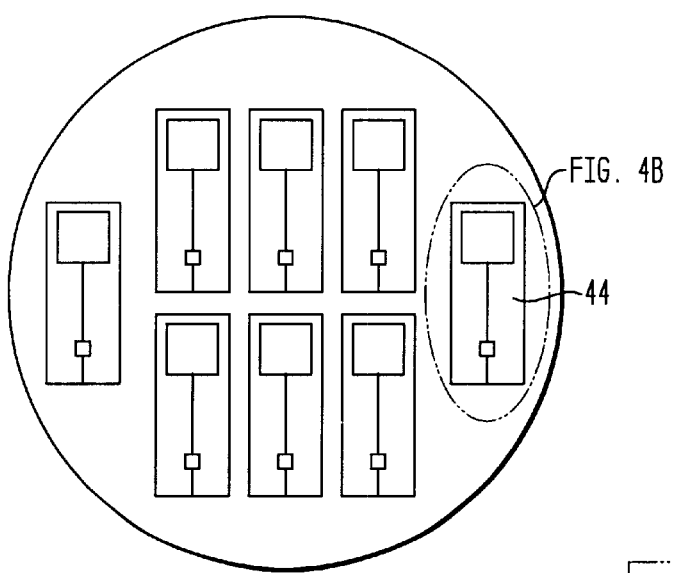
FIG. 4a is a schematic view of an array of micromechanical modules formed on a silicon wafer.

FIG. 4a shows schematically a silicon wafer on which an array of micromechanical modules 44 has been formed. Each of such modules can be used as a component of a second embodiment 41 of a micromechanical pipetting module according to the invention.

Figure 4B:
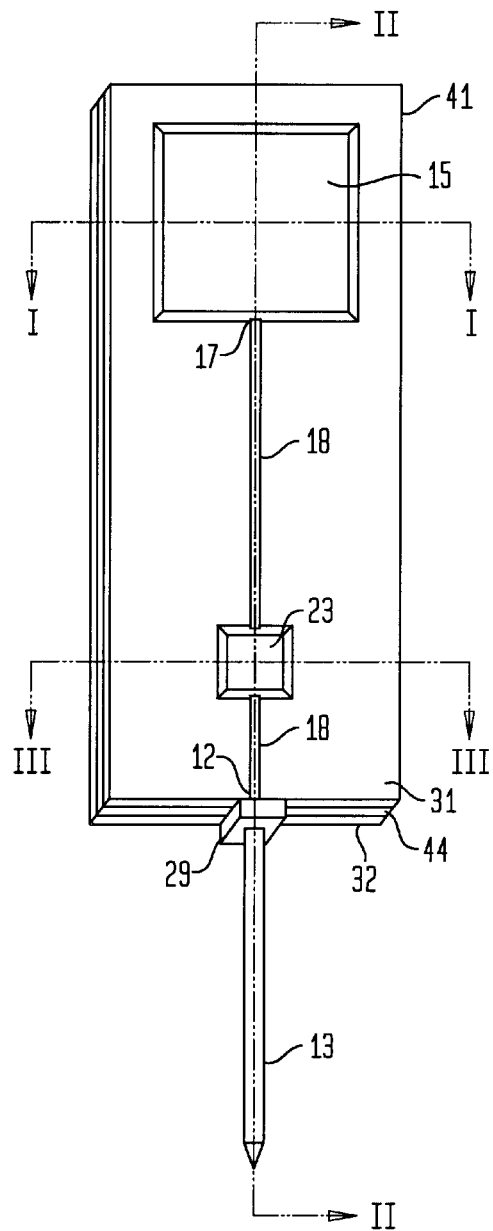
FIG. 4b is a schematic view of a second embodiment of a micromechanical pipetting module according to the invention.

FIG. 4b shows schematically a second embodiment 41 of a micromechanical pipetting module according to the invention. Liquid volumes in a range between a minimum value smaller than a microliter and a maximum value of about 10 microliters can be pipetted with such a module. Module 41 is an integrally built pipetting module comprising a micromechanical structure which is integrally built on a silicon wafer 14.

As can be appreciated from FIG. 4b micromechanical pipetting module 41 is very similar to micromechanical pipetting module 11 shown by FIG. 1, but differs therefrom in that in module 41 a portion of the channel 18 forms a chamber 23.

Figure 5:
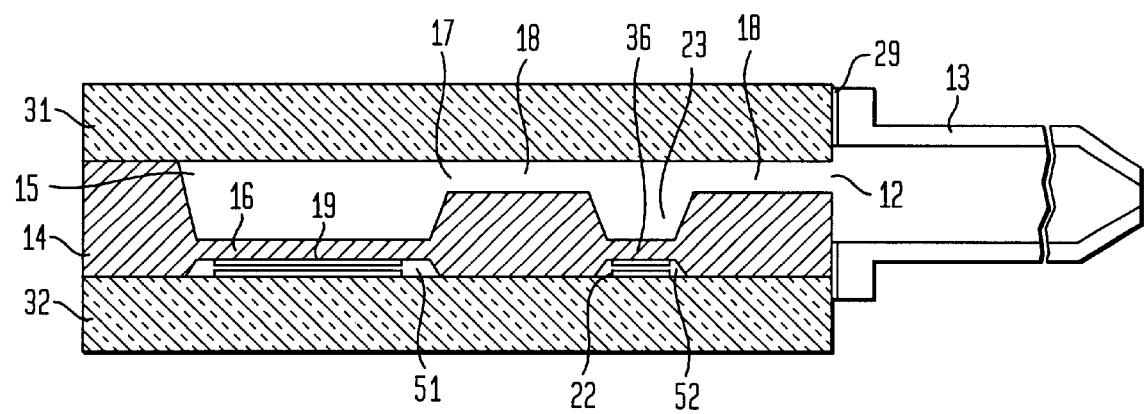
FIG. 5 is a partial representation of a longitudinal section along the line II—II in FIG. 4b.

FIG. 5 shows a longitudinal section of micromechanical pipetting module 41 shown by FIG. 4b. Micromechanical pipetting module 41 shown by FIG. 5 comprises chamber 15 having membrane 16 as bottom wall, channel 18, actuator means 19 for displacing membrane 16, a chamber 23 formed by a portion of channel 18, and sensor means 22 for generating an output signal related to the displacement of the membrane 16. A portion of channel 18 is part of sensor means 22 and the output signal generated by this sensor means is related to the displacement of membrane 16. Components of actuator means 19 are located in chamber 51 delimited by membrane 16, silicon wafer 14 and glass plate 32. Components of sensor 22 are located in a chamber 52 delimited by a membrane 36 which is part of silicon wafer 14, silicon wafer 14 and glass plate 32.

Sensor 22 is for instance a pressure sensor or a flow measurement sensor. Sensor 22 in FIG. 5 is pressure sensor comprising an electrical capacitor as measuring element. Sensor 22 can also be a piezoresistive sensor or any other type of pressure sensor.

Sensor 22 can also be used for liquid level detection before aspiration of liquid to be pipetted.

Figure 6:
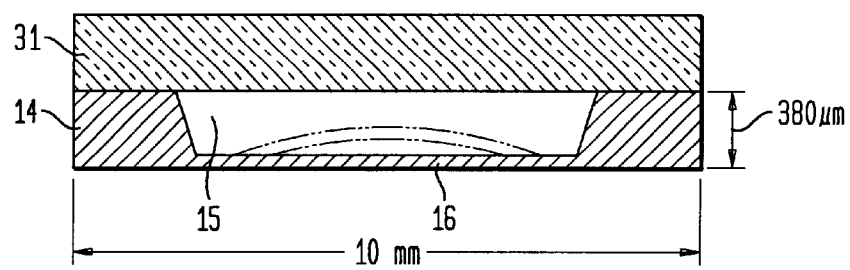
FIG. 6 is a partial representation of a cross-section along the line I—I in FIG. 4b.

FIG. 6 shows a partial representation of a cross-section along the line I—I in FIG. 1b. FIG. 6 shows in particular the cross-sectional shape of chamber 15 and an example of the width and depth of wafer layer 14 of pipetting module 41. The broken line in FIG. 6 shows the position taken by the membrane 16 when it is displaced e.g. by means of an actuator located below membrane 16, but not represented in FIG. 6.

Figure 7:
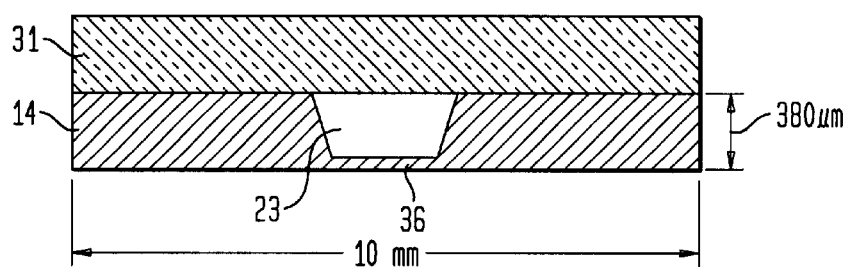
FIG. 7 is a partial representation of a cross-section along the line III—III in FIG. 4b.

FIG. 7 shows a partial representation of a cross-section on the line III—III in FIG. 4b. FIG. 7 shows in particular the cross-sectional shape of chamber 23 of module 41.

The operation of micromechanical pipetting module 41 is very similar to the operation of module 11 described above with reference to FIGS. 1a, 1b, 2 and 3 with exception of the fact that in module 41 sensor 22 for producing an output signal related to the displacement of membrane 16 is located under chamber 23, that is at a distance from membrane 16, whereas in module 11 sensor 21 for producing such an output signal is located under chamber 15 and directly under membrane 16.

Figure 8:
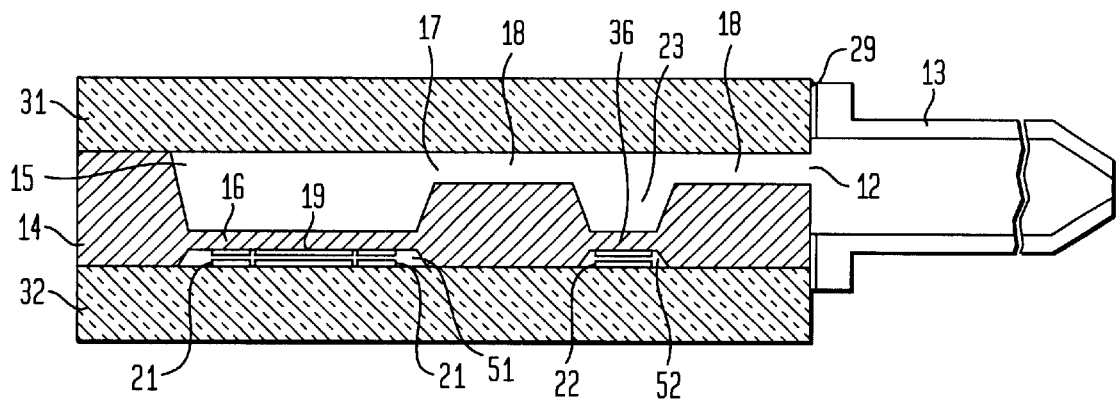
FIG. 8 is a longitudinal section of a third embodiment of a micromechanical pipetting module according to the invention.

FIG. 8 shows a longitudinal section of a third embodiment of a micromechanical pipetting module according to the invention obtained by modifying the embodiment shown by FIG. 5. The embodiment shown by FIG. 8 differs from the embodiment shown by FIG. 5 in that the embodiment shown by FIG. 8 comprises an additional sensor 21 located adjacent to actuator 19 in chamber 51. Like in the embodiment shown by FIG. 2., Sensor 21 in FIG. 8 is preferably a displacement sensor. Sensor 21 in FIGS. 2, 8, 9 and 10 is a displacement sensor comprising an electrical capacitor as measuring element. Sensor 21 in FIGS. 2, 8, 9 and 10 can be replaced by an electro-optical sensor.

Figure 9:
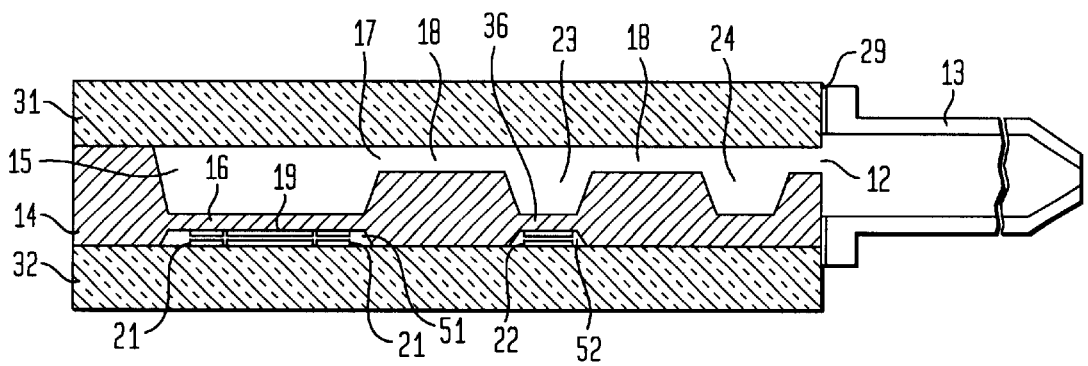
FIG. 9 is a longitudinal section of a fourth embodiment of a micromechanical pipetting module according to the invention.

FIG. 9 shows a longitudinal section of a fourth embodiment of a micromechanical pipetting module according to the invention obtained by modifying the embodiment shown by FIG. 8. In addition to the features of the embodiment shown by FIG. 8, in the embodiment shown by FIG. 9 a portion of the channel 18 forms a third chamber 24 which is located between outlet 12 of the pipetting module and chamber 23. Chamber 24 serves to prevent pipetted fluid from contacting the portion of the channel 18 which comprises sensor 22.

In a modified version of the embodiment shown by FIG. 2 a chamber similar to chamber 24 in FIG. 9 is located between outlet 12 of the pipetting module and chamber 15. Such a modified version is not represented in the drawings.

Figure 10:
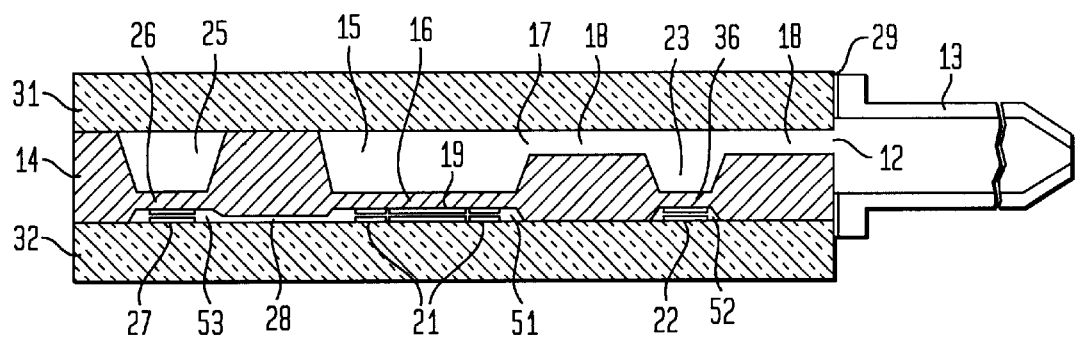
FIG. 10 is a longitudinal section of a fifth embodiment of a micromechanical pipetting module according to the invention.

FIG. 10 shows a longitudinal section of a fourth embodiment of a micromechanical pipetting module according to the invention obtained by modifying the embodiment shown by FIG. 8. In addition to the features of the embodiment shown by FIG. 8, the embodiment shown by FIG. 10 has an additional pressure sensor 27 for measuring the pressure on the actuator side, that is in channel 28 and in the chambers fluidically connected therewith, and an additional chamber 25 delimited by a membrane 26 which is part of silicon wafer 14, silicon wafer 14 and glass plate 31. Chamber 25 located above membrane 26 is a reference chamber for the operation of sensor 27. Channel 28 connects a chamber 53 where pressure sensor 27 is located with the chamber 51 where actuator 19 is located. Pressure sensor 27 is used for monitoring the pressure applied in the case of pneumatic actuation principle, according to which a certain pressure is maintained in the actuator chamber, e.g. by thermopneumatic actuation. This pressure differs from the pressure measured by sensor 22 in that the signal of sensor 22 is modulated by the dynamics and the force of the actuator membrane and the fluidic behavior (i.e. dynamics and gravity) of the aspirated sample liquid and of the system fluid. Sensor 27 is used as part of a control system for maintaining a given (static) pressure by a direct feedback system and monitoring the behavior of the liquid by means including sensors 21, 22 and 27 analyzing the signals obtained with these sensors and if necessary feeding back a correction signal to the primary control system. The advantage of the supplementary pressure sensor 27 over displacement sensor 21 which measures the displacement of membrane 16 is that the output signal provided by sensor 27 is independent from the pressure in the channel system formed e.g. by chamber 15, channel 18 and chamber 23 in the embodiment shown by FIG. 8, which pressure is measured by sensor 22, and it is independent from temperature changes of membrane 16 and its environment, temperature changes which can be caused, for example, by a thermopneumatic actuation of membrane 16.

In addition to one or more micromechanical pipetting modules of the type described above, a micromechanical pipetting device according to the invention comprises control means (not represented in the enclosed drawings) for controlling the operation of the actuator means 19 in response to one or more output signals generated by sensor means which produce an output signal representative of the displacement of membrane 16 for effecting pipetting operations. Such output signals are for instance the output signal of sensor 21 in FIGS. 2, 8 and 9, the output signal of sensor 22 in FIGS. 5, 8 and 9, and the output signal of sensor 27 in FIG. 10.

In the preferred embodiment described above with reference to FIGS. 1a, 1b, 2 and 3 the control means control the operation of the actuator means 19 in response to the output signal generated by sensor means 21.

In the preferred embodiment described above with reference to FIGS. 4a, 4b, and 5 to 7 the control means control the operation of the actuator means 19 in response to the output signal generated by sensor means 22.

In the preferred embodiments described above with reference to FIGS. 8 and 9 the control means control the operation of the actuator means 19 in response to the output signals generated by sensor means 21 and 22.

In the preferred embodiment described above with reference to FIG. 10 control means control the operation of the actuator means 19 in response to the output signals generated by sensor means 21, 22 and 27.

In a preferred embodiment of the invention the micropipetting module 11 and the means for controlling the operation of the actuator means 19 are so configured and dimensioned that the total volume to be aspirated and dispensed with the pipetting tip 13 is aspirated into the pipetting tip 13 by means of a single stroke of the displacement movement of the membrane 16.

The control means for controlling the operation of the actuator means 19 may be at least partially integrated in the structure of a micropipetting module according to the invention or they may be partially or to a large extent located outside the micropipetting module.

According to a further aspect of the invention several sensors like 21, 22 and 27 optimized for different measuring ranges can be integrated into a compact micropipetting module according to the invention.

According to a further aspect of the invention combined use of the output signals provided by sensors 21, 22 and 27 improves the reliability in the interpretation of the signals provided by the sensors and enables active monitoring of the liquid dispensed, which is important in order to avoid malfunctions of the micropipetting module, which can occur for instance due to clotting of the pipetting tip. Pipetting of air bubbles, which has to be avoided in medical diagnosis tests, can be detected by the use of pressure sensors, before the test is performed. Processing of information obtained with the pressure sensors during aspiration of the sample allows recognition of highly viscous patient samples. These pathogen samples often represent a problem for the correct interpretation of medical test results.

According to a further aspect of the invention a plurality of micromechanical pipetting modules like the above described modules 11 or 41 are integrally built on a silicon wafer 14.

According to a further aspect of the invention, pipetting tip 13 is a silicon pipetting tip integrally built with the pipetting module 11 or 41.

What is claimed is:

1. A micromechanical pipetting device comprising a pipetting module which has an inlet/outlet which is connectable to a pipetting tip, wherein said pipetting module is integrally built on a silicon wafer and comprises
    a) a first chamber located within said pipetting module, wherein at least a portion of one wall of the chamber comprises a displaceable membrane adapted to alter the volume of the chamber, said first chamber having one opening to allow fluid flow into and from the interior of said first chamber,
    b) a channel located within said pipetting module, said channel establishing a direct, valveless and permanent fluid connection between said opening of the first chamber and the inlet/outlet of the pipetting module,
    c) actuator means for displacing said membrane, and thereby aspirating or expelling a volume of air or liquid into or out of said first chamber, which in turn causes aspiration or expulsion of a volume of a liquid sample from said pipetting tip,
    d) first sensor means disposed outside of said first chamber and said channel for generating a first output signal related to the displacement of the membrane and
    wherein a portion of the channel forms a second chamber and is part of a second sensor means for generating a second output signal representative of the pressure in the channel, and the means for controlling the operation of the actuator means is responsive to both the first and second output signals.

2. A micromechanical pipetting device comprising a pipetting module which has an inlet/outlet which is connectable to a pipetting tip, wherein said pipetting module is integrally built on a silicon wafer and comprises
    a) a first chamber located within said pipetting module, wherein at least a portion of one wall of the chamber comprises a displaceable membrane adapted to alter the volume of the chamber, said first chamber having one opening to allow fluid flow into and from the interior of said first chamber,
    b) a channel located within said pipetting module, said channel establishing a direct, valveless and permanent fluid connection between said opening of the first chamber and the inlet/outlet of the pipetting module,
    c) actuator means for displacing said membrane, and thereby aspirating or expelling a volume of air or liquid into or out of said first chamber, which in turn causes aspiration or expulsion of a volume of a liquid sample from said pipetting tip, d) first sensor means disposed outside of said first chamber and said channel for generating a first output signal related to the displacement of the membrane and wherein a portion of the channel forms a second chamber and is part of a second sensor means for generating a second output signal representative of the fluid flow through the channel, and the means for controlling the operation of the actuator means is responsive to both the first and second output signals.

3. A micromechanical pipetting device according to claim 1, wherein a portion of the channel forms a third chamber which is located between the pipetting tip and the first or the second sensor means, said third chamber serving for preventing pipetted fluid from contacting the portion of the channel which comprises said first sensor means or said second sensor means.

4. A micromechanical pipetting device according to claim 1, wherein said second sensor means comprises a pressure or a flow measurement sensor.

5. A micromechanical pipetting device according to claim 1, wherein a plurality of said pipetting modules is integrally built on a silicon wafer.

6. A micromechanical pipetting device according to claim 3, wherein a plurality of said pipetting modules is integrally built on a silicon wafer.

7. A micromechanical pipetting device according to claim 1, wherein the pipetting tip is a silicon pipetting tip integrally built with the pipetting module.

8. A micromechanical pipetting device according to claim 3, wherein the pipetting tip is a silicon pipetting tip integrally built with the pipetting module.

9. A micromechanical pipetting device which has an inlet/outlet connectable to a pipetting tip, and said device comprises a) a first chamber wherein at least a portion of one wall of the chamber comprises a displaceable membrane adopted to alter the volume of the chamber, said first chamber having an opening to allow fluid flow into and from the interior of said first chamber, b) a channel for establishing a fluid connection between said opening of the first chamber and the inlet/outlet of the pipetting module, c) actuator means for displacing said membrane, and thereby aspirating or expelling a volume of air or liquid into or out of said first chamber, which in turn causes aspiration or expulsion of a volume of a liquid sample from said pipetting tip, and d) first sensor means disposed outside of said first chamber and said channel for generating a first output signal related to the displacement of the membrane.

10. A micromechanical pipetting device according to claim 9 further comprising control means for controlling the operation of the actuator means in response to the first output signal generated by the first sensor means.

11. A micromechanical pipetting device according to claim 9, wherein the micropipetting module and the means for controlling the operation of the actuator means are so configured and dimensioned that the total volume to be aspirated and dispensed with the pipetting tip is aspirated into the pipetting tip by means of a single stroke of the displacement movement of the membrane.

12. A micromechanical pipetting device according to claim 9, wherein said first sensor means is responsive to the membrane.

13. A micromechanical pipetting device according to claim 9, wherein said channel is defined by walls and said first sensor means is responsive to a portion of these walls.

14. A micromechanical pipetting device according to claim 9, wherein said sensor means generates an output signal representative of the pressure in said chamber.

15. A micromechanical pipetting device according to claim 9, wherein said actuator means comprises an electrostatic actuator.

16. A micromechanical pipetting device according to claim 9, wherein said actuator means comprises a piezoelectric actuator.

17. A micromechanical pipetting device according to claim 9, wherein said membrane is displaced by thermopneumatic means.

18. A micromechanical pipetting device according to claim 9, wherein said first sensor means is a capacitive sensor.

19. A micromechanical pipetting device according to claim 9, wherein said first sensor means is an electro-optical sensor.

20. A micromechanical pipetting device according to claim 9, wherein a plurality of said pipetting modules is integrally built on a silicon wafer.

21. A micromechanical pipetting device according to claim 9, wherein the pipetting tip is a silicon pipetting tip integrally built with the pipetting module.

22. A micromechanical pipetting device according to claim 9, wherein said fluid includes a liquid.

23. A micromechanical pipetting device according to claim 9, wherein said fluid includes a gas.

24. A micromechanical pipetting device according to claims 9, wherein said fluid includes a liquid and a gas.

25. The device of claim 9 wherein said device comprises a pipetting module and said channel is disposed in said module.

26. The device of claim 25 wherein said chamber is disposed in said module.

27. The device of claim 25 wherein said module is integrally fabricated on a silicon wafer.

* * * * *